(12) United States Patent
Katsuyama

(10) Patent No.: US 10,349,920 B2
(45) Date of Patent: Jul. 16, 2019

(54) ULTRASOUND DIAGNOSTIC DEVICE, SOUND VELOCITY DERIVATION METHOD AND PROGRAM

(71) Applicant: FUJIFILM CORPORATION, Minato-ku, Tokyo (JP)

(72) Inventor: Kimito Katsuyama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 641 days.

(21) Appl. No.: 14/535,316

(22) Filed: Nov. 6, 2014

(65) Prior Publication Data

US 2015/0065880 A1   Mar. 5, 2015

Related U.S. Application Data

(63) Continuation of application No. PCT/JP2013/064397, filed on May 23, 2013.

(30) Foreign Application Priority Data

May 25, 2012   (JP) ................................. 2012-120242

(51) Int. Cl.
*A61B 8/14*   (2006.01)
*A61B 8/08*   (2006.01)
(Continued)

(52) U.S. Cl.
CPC ............ *A61B 8/5269* (2013.01); *A61B 8/145* (2013.01); *A61B 8/4483* (2013.01);
(Continued)

(58) Field of Classification Search
None
See application file for complete search history.

(56) References Cited

U.S. PATENT DOCUMENTS 4,835,689 A * 5/1989 O'Donnell .......... G01S 7/52049
250/580
5,415,173 A * 5/1995 Miwa .................. G01S 7/52049
600/447

(Continued)

FOREIGN PATENT DOCUMENTS

| JP | H09-224938 A | 9/1997 |
| JP | 2001-252276 A | 9/2001 |
| JP | 2007-7045 A | 1/2007 |

OTHER PUBLICATIONS

Machine translation of JP H09-224938 A.*

(Continued)

*Primary Examiner* — Pascal M Bui Pho
*Assistant Examiner* — Colin T. Sakamoto
(74) *Attorney, Agent, or Firm* — SOLARIS Intellectual Property Group, PLLC

(57) ABSTRACT

An estimated value of sound velocity of a subject interior is derived more stably and with higher accuracy. A phasing processing section provides, to each of received signals that were generated by piezoelectric elements respectively, respective delay times that were computed on the basis of each of plural set sound velocities, and phases the received signals per set sound velocity. A degree of similarity deriving section derives, for each of the set sound velocities, a degree of mutual similarity among received signals that were phased by the phasing processing section. An optimal set sound velocity deriving section derives, as an optimal set sound velocity, an estimated value of sound velocity of the subject interior on the basis of the degree of mutual similarity among the received signals of each of the set sound velocities.

19 Claims, 5 Drawing Sheets

(51) Int. Cl.
  *A61B 8/00*     (2006.01)
  *G01S 7/52*     (2006.01)
(52) U.S. Cl.
  CPC .......... *A61B 8/4494* (2013.01); *A61B 8/5207* (2013.01); *G01S 7/52036* (2013.01); *G01S 7/52049* (2013.01); *G01S 7/52077* (2013.01); *A61B 8/14* (2013.01); *A61B 8/488* (2013.01)

(56) References Cited

U.S. PATENT DOCUMENTS

| | | | | |
|---|---|---|---|---|
| 5,741,979 | A * | 4/1998 | Arndt ...................... | G01F 1/708 324/639 |
| 2004/0210137 | A1* | 10/2004 | Baba ................... | G01S 7/52034 600/443 |
| 2006/0100666 | A1* | 5/2006 | Wilkinson ............... | A61B 5/08 607/1 |
| 2009/0099455 | A1* | 4/2009 | Katsuyama .............. | A61B 8/00 600/459 |

OTHER PUBLICATIONS

Partial English language translation of the following: Office Action dated Oct. 20, 2015 from the JPO in a Japanese patent application corresponding to the instant patent application.
International Search Report issued in International Application No. PCT/JP2013/064397 dated Aug. 13, 2013.
Written Opinion of the ISA issued in International Application No. PCT/JP2013/064397 dated Aug. 13, 2013.

* cited by examiner

ULTRASOUND DIAGNOSTIC DEVICE, SOUND VELOCITY DERIVATION METHOD AND PROGRAM

CROSS-REFERENCE TO RELATED APPLICATIONS

This application is a continuation application of International Application No. PCT/JP2013/064397, filed May 23, 2013, the disclosure of which is incorporated herein by reference in its entirety. Further, this application claims priority from Japanese Patent Application No. 2012-120242, filed May 25, 2012, the disclosure of which is incorporated herein by reference in its entirety.

TECHNICAL FIELD

The present invention relates to an ultrasonic diagnostic device, a sound velocity derivation method and a program stored on a computer-readable storage medium that generate tomographic images of a subject by transmitting and receiving ultrasonic waves.

RELATED ART

There are known ultrasonic diagnostic devices that transmit ultrasonic waves to a subject from an ultrasonic probe, and, on the basis of reflected waves from the subject interior, generate tomographic images of the subject. In an electronic scanning type ultrasonic diagnostic device, when ultrasonic waves are transmitted, transmission focusing is carried out that supplies driving pulse signals, that have delay time differences corresponding to the arrangement of respective electroacoustic conversion elements of the ultrasonic probe, to the respective electroacoustic conversion elements and offset the transmission timings of the ultrasonic waves among the elements. On the other hand, at the time of receiving the reflected waves, receive focusing is carried out that provides delay times, that correspond to the arrangement of the respective electroacoustic conversion elements, to the respective received signals that are generated at the respective electroacoustic conversion elements, and makes uniform the time phases of the respective received signals. Due thereto, the azimuth resolution of the ultrasound images can be improved.

The delay times that are provided to the respective signals at the times of transmitting and receiving ultrasonic waves are set on the basis of the distances from the respective electroacoustic conversion elements to the focal point, and the sound velocity of the propagation medium. Usually, a hypothetical sound velocity that has been supposed is used as the sound velocity of the propagation medium. However, in living body tissue that is the propagation medium, the sound velocity differs in accordance with the region thereof. Therefore, if a difference arises between the actual sound velocity and the hypothetical sound velocity that is used in order to set the delay times, a focal point cannot be formed properly in both transmission and reception, which leads to a deterioration in image quality. With regard to this problem, techniques for estimating the actual sound velocity on the basis of the received signals and improving image quality of the ultrasound images are disclosed in the following patent documents.

For example, Japanese Patent Application Laid-Open (JP-A) No. 2007-7045 (Patent Document 1) discloses generating plural beam profiles, at which the set sound velocities differ, from echo signals that are phased and added, and displaying the plural generated beam profiles so as to be superposed on a same screen, and selecting, as the sound velocity of the living body, the sound velocity corresponding to the beam profile that has the smallest beam width among the beam profiles.

Further, JP-A No. 2001-252276 (Patent Document 2) discloses carrying out trial irradiation of ultrasonic waves into a living body at a delay time corresponding to an average sound velocity, and determining a delay time error by computation from signals of respective channels that are obtained by delay-controlling the received signals thereof, and comparing the determined data with delay time error data of plural sound velocities whose parameters are sound velocities that have been stored in advance, and determining the sound velocity, that corresponds to the coincident delay time thereamong, as the sound velocity within the living body.

In accordance with the technique disclosed in above-described Patent Document 1, after phasing and adding processing is carried out on the received signals by using plural set sound velocities, much time is needed for processing in order to make the ultrasonic wave intensity distribution into an image.

On the other hand, in the technique of Patent Document 2, the delay time error is determined by computation from echo signals of respective channels that have been delay-controlled. However, it is not easy to stably carry out measurement of delay time errors between channels. Namely, if a decrease in intensity or waveform distortion arises due to the ultrasonic waves that are transmitted within the living body interfering or the like, the accuracy of measurement of the delay time error deteriorates markedly. As a result, the accuracy of estimating the actual sound velocity within a living body deteriorates.

SUMMARY OF INVENTION

The present invention was made in consideration of the above-described points, and an object thereof is to provide an ultrasonic diagnostic device, a sound velocity derivation method and a program stored on a computer-readable storage medium that can more stably and highly accurately derive an estimated value of sound velocity of a subject interior.

An ultrasonic diagnostic device according to an aspect of the present invention includes: plural electroacoustic conversion elements that respectively generate received signals in accordance with reflected waves of ultrasonic waves that were transmitted to a subject interior; a degree of similarity deriving section for deriving, for each of plural set sound velocities, a degree of mutual similarity that is derived on the basis of a set sound velocity and that expresses similarity among the received signals in each of time regions of the received signals; and a sound velocity deriving section for deriving an estimated value of sound velocity of the subject interior on the basis of the degree of mutual similarity of each of the plural set sound velocities that was derived by the degree of similarity deriving section.

A sound velocity deriving method according to an aspect of the present invention includes: a step of phasing, for each of plural set sound velocities, plural received signals that were generated respectively by plural electroacoustic conversion elements in accordance with reflected waves of ultrasonic waves transmitted to a subject interior; a step of deriving, for each of the plural set sound velocities, a degree of mutual similarity that expresses similarity among received signals of the plural received signals that were phased; and a step of deriving an estimated value of sound velocity of the subject interior on the basis of the degree of mutual similarity of each of the plural set sound velocities.

A non-transitory computer-readable storage medium according to an aspect the present invention stores a program that causes a computer to function as: phasing section for, for each of plural set sound velocities, phasing plural received signals that were generated respectively by plural electroacoustic conversion elements in accordance with reflected waves of ultrasonic waves transmitted to a subject interior; degree of similarity deriving section for, for each of the plural set sound velocities, deriving a degree of mutual similarity that expresses similarity among received signals of the plural received signals that were phased by the phasing section; and sound velocity deriving section for deriving an estimated value of sound velocity of the subject interior on the basis of the degree of mutual similarity of each of the plurality of set sound velocities that was derived by the degree of similarity deriving section.

DETAILED DESCRIPTION

Figure 1:
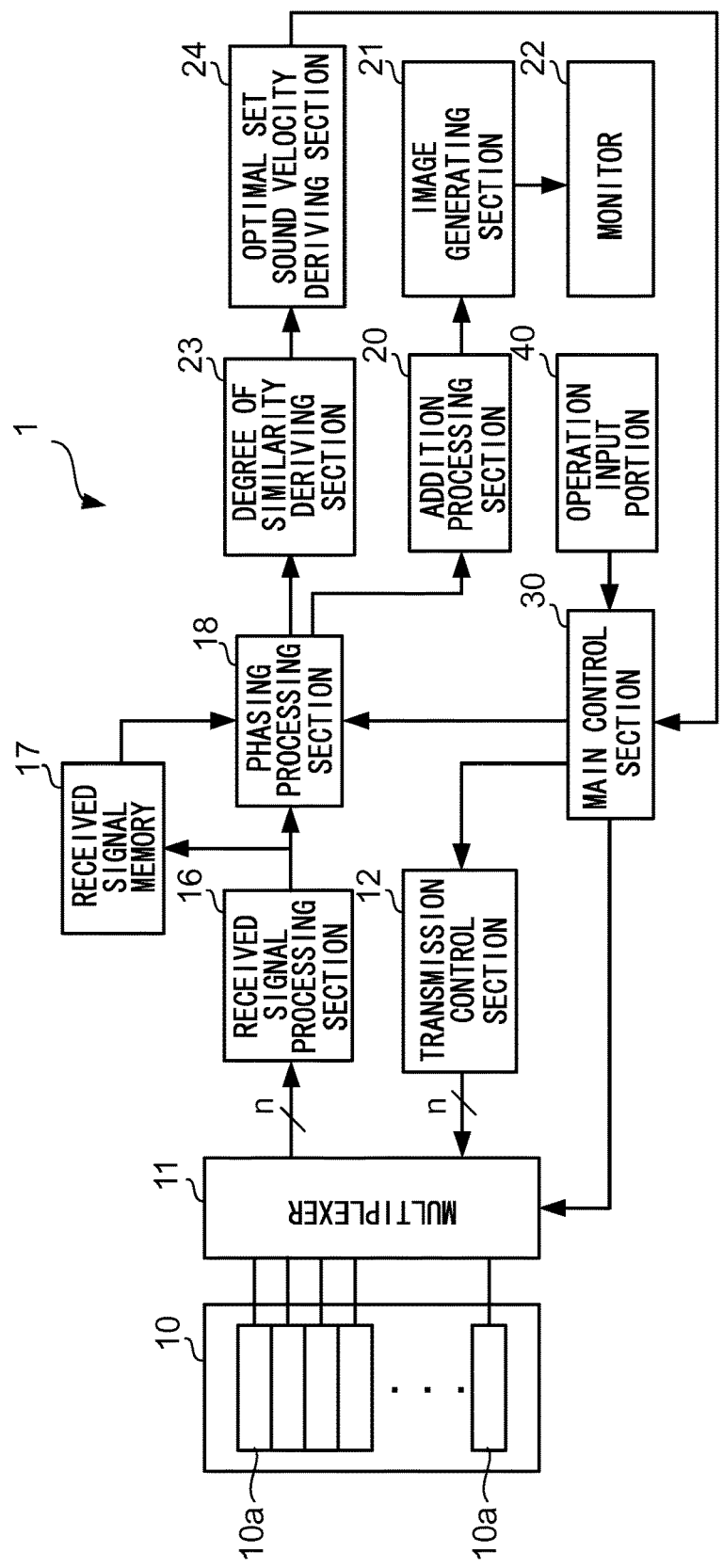
FIG. 1 is a block diagram showing the structure of an ultrasonic diagnostic device relating to an embodiment of the present invention.

An embodiment of the present invention is described hereinafter with reference to the drawings. Note that, in the respective drawings, structural elements or portions that are substantially the same or equivalent are denoted by the same reference numerals.

FIG. 1 is a block diagram showing the structure of an ultrasonic diagnostic device 1 relating to the embodiment of the present invention.

An ultrasonic probe 10 is a probe that transmits ultrasonic waves toward a region to be diagnosed of a subject, and receives ultrasonic waves that have been reflected at the interior of the subject. The ultrasonic probe 10 includes m piezoelectric elements 10a that serve as electroacoustic conversion elements and are arrayed rectilinearly. A one-time transmission/receiving of ultrasonic waves is carried out by using a group of adjacent n (m>n) piezoelectric elements that are selected from among the m piezoelectric elements 10a. By successively shifting the group of n piezoelectric elements that are used in the transmission/receiving of ultrasonic waves, the region to be diagnosed that is within the subject is scanned by an ultrasonic beam. Note that the ultrasonic probe 10 may be a probe having a scanning system that is any of a linear type, a convex type, a sector type or the like. The respective piezoelectric elements 10a are connected to a multiplexer 11 via signal lines of m channels. The respective piezoelectric elements 10a generate ultrasonic waves in accordance with driving pulse signals that are supplied from a transmission control section 12 via the multiplexer 11. Further, the respective piezoelectric elements 10a receive ultrasonic waves that have been reflected at the interior of the subject, and generate received signals that are electric signals, and supply these to a received signal processing section 16 via the multiplexer 11.

The multiplexer 11 is an electronic switch that, in accordance with control signals that are supplied from a main control section 30, selects the group of n adjacent piezoelectric elements that are used in the transmission/receiving of ultrasonic waves, from among the m piezoelectric elements 10a of the ultrasonic probe 10. The multiplexer 11 is connected to the transmission control section 12 and the received signal processing section 16 via signal lines of n channels.

In accordance with control signals supplied from the main control section 30, the transmission control section 12 generates driving pulse signals of n channels. Further, the transmission control section 12 provides a time difference to the driving pulse signal per channel, in order to carry out transmission focusing that converges the ultrasonic beam at the depth position of a region of interest that has been designated by the main control section 30. The driving pulse signals that are generated at the transmission control section 12 are supplied respectively to the n piezoelectric elements 10a that are selected by the multiplexer 11.

The received signal processing section 16 has amplifiers and A/D converters that are provided per channel. The respective received signals, that are generated at the n piezoelectric elements 10a that are selected by the multiplexer 11, are amplified at the amplifiers, and are converted into digital signals by the A/D converters.

A received signal memory 17 is a storage medium that stores, as received data, the received signals of the respective channels that have been converted into digital signals by the received signal processing section 16.

In order to phase the respective received signals, a phasing processing section 18 computes relative time differences among the received signals, on the basis of a set sound velocity that is supplied from the main control section 30. Further, the phasing processing section 18 carries out phasing processing, i.e., receive focusing processing, that makes uniform the time phases of the received signals of the respective channels by providing the computed relative time differences to the received signals of the respective channels that are supplied from the received signal processing section 16 or the received signal memory 17. The timings at which ultrasonic waves, that are reflected at a given spot within the subject, are incident on the respective piezoelectric elements 10a do not coincide. This is because the propagation distances of the ultrasonic waves that reach the respective piezoelectric elements 10a from the reflection point differ per piezoelectric element. The phasing processing section 18 provides relatively long delay times to the received signals that are generated by the piezoelectric elements that are disposed at positions where the distances to the reflection point are relatively short. On the other hand, the phasing processing section 18 provides relatively short delay times to the received signals that are generated by the piezoelectric elements that are disposed at positions where the distances to the reflection point are relatively long. Due thereto, the phasing processing section 18 carries out phasing processing that makes uniform the time phases of the received signals of the respective channels.

An addition processing section 20 sums the received signals of the respective channels that have been phased by the phasing processing section 18, and generates a phased and added signal.

An image generating section 21 carries out filtering processing, Log compression processing, envelope detection processing, STC (Sensitivity Time Control) processing, interpolation processing, scan conversion processing, and the like on phased and added signals that are supplied from the addition processing section 20, and generates image signals for constructing so-called B-mode images in which the signal intensities of the phased and added signals are converted into brightnesses.

A monitor 22 is a display device such as a liquid crystal display panel or the like that displays tomographic images or the like of the region to be diagnosed, on the basis of the image signals generated by the image generating section 21. A degree of similarity deriving section 23 derives a degree of mutual similarity that is an index value expressing the similarity among the received signals of the respective channels that the phasing processing section 18 has phased on the basis of the set sound velocity. Namely, the degree of mutual similarity is an index value that expresses the similarity on the whole of the received signals of the respective channels that have been phased on the basis of the set sound velocity. For example, for each of plural regions that are objects of computation that are divided in the time axis direction of the received signal (i.e., the depth direction in the imaging region), the degree of similarity deriving section 23 derives correlation values between a template signal $St(t)$ that is a comparison reference that is described later and received signals $S1(t)$ through $Sn(t)$ of the respective channels, respectively (refer to FIG. 3 for both). Then, on the basis of the computed correlation values, the degree of similarity deriving section 23 derives a degree of mutual similarity per region that is an object of computation (per depth region). For example, a signal obtained by phasing and adding of the received signals of the respective channels can be used as the template signal that is the comparison reference.

In a case in which the set sound velocity, that the phasing processing section 18 uses at the time of phasing the received signals of the respective channels, substantially coincides with the actual sound velocity of the interior of the subject, the time phases of the received signals of the respective channels are uniform, and therefore, the value of the degree of mutual similarity that is derived at the degree of similarity deriving section 23 is high. As the difference between the actual sound velocity at the interior of the subject and the set sound velocity that the phasing processing section 18 uses at the time of phasing the received signals of the respective channels becomes larger, the offset in the time phases among the received signals becomes larger, and therefore, the value of the degree of mutual similarity that is derived at the degree of similarity deriving section 23 becomes lower.

On the basis of the degree of mutual similarity of a received signal group that was derived for each of the plural set sound velocities at the degree of similarity deriving section 23, an optimal set sound velocity deriving section 24 derives an optimal set sound velocity, that is an estimated value of the actual sound velocity within the subject, for each unit region within the imaging region that corresponds to the region that is the object of computation of the above-described degree of mutual similarity. The optimal set sound velocity deriving section 24 may derive, for example, the set sound velocity at which the degree of mutual similarity of the received signal group is the highest, as the optimal set sound velocity at that unit region.

The main control section 30 carries out general control of the transmitting/receiving processings of ultrasonic waves by providing control signals to the multiplexer 11, the transmission control section 12, and the phasing processing section 18.

An operation input portion 40 is a portion that receives various types of operation inputs by a user, and is a portion that is structured by, for example, a pointing device such as a mouse or the like and input means such as a keyboard or the like.

Figure 2:
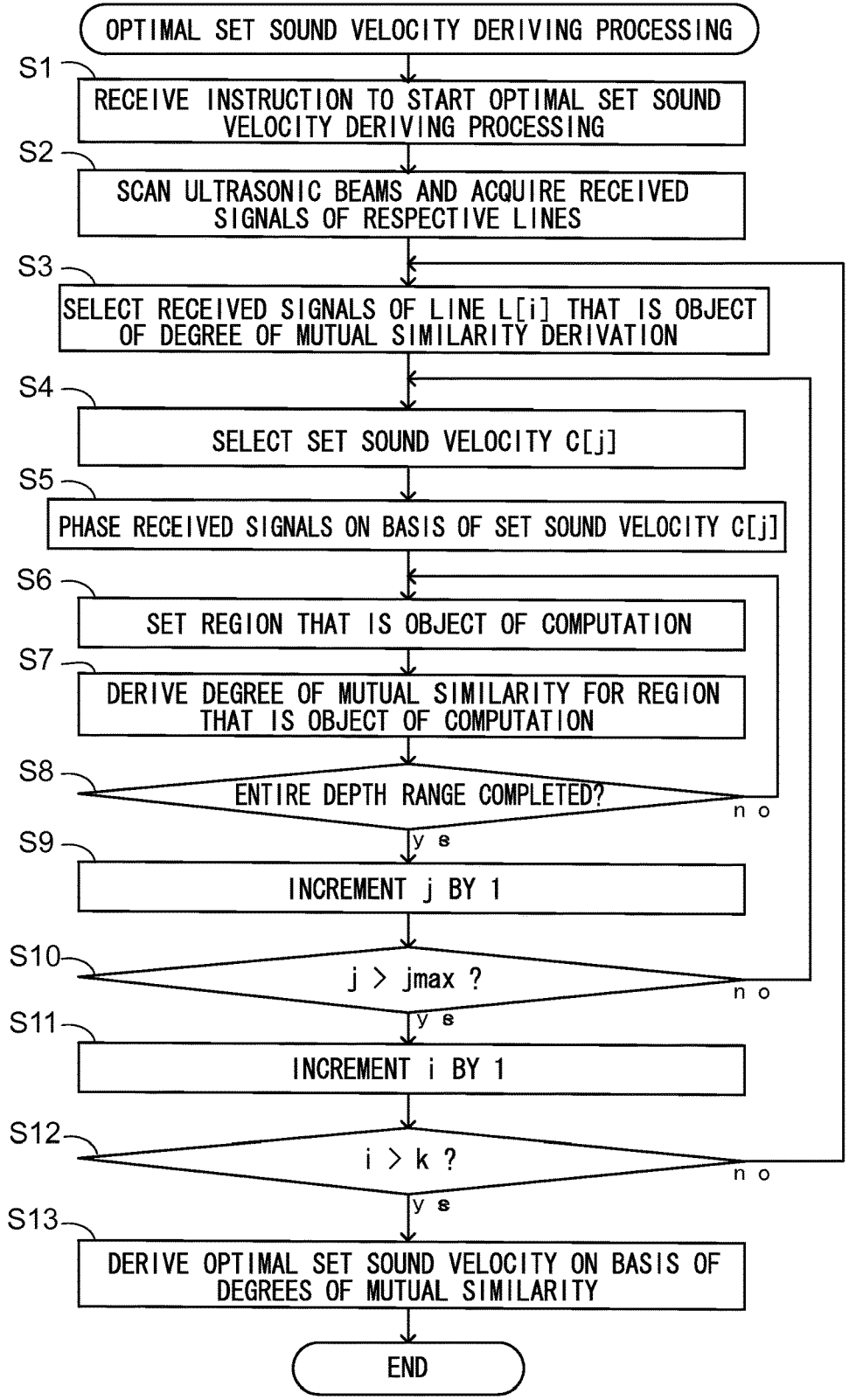
FIG. 2 is a flowchart showing the flow of an optimal set sound velocity deriving processing program that is executed at the ultrasonic diagnostic device relating to the embodiment of the present invention.

Note that the transmission control section 12, the received signal processing section 16, the phasing processing section 18, the addition processing section 20, the image generating section 21, the degree of similarity deriving section 23, the optimal set sound velocity deriving section 24, and the main control section 30 can be structured by a computer having a ROM that serves as a storage medium that stores a program reciting the respective processings of an optimal set sound velocity deriving processing routine that is shown in FIG. 2 and is described hereinafter, a CPU for executing this program, a RAM for temporarily storing contents of processing at the CPU, and the like.

Processings by which the ultrasonic diagnostic device 1 relating to the present embodiment derives an optimal set sound velocity within a subject are described next with reference to the flowchart shown in FIG. 2.

When the user carries out an operation from the operation input portion 40 to start the processing of deriving the optimal set sound velocity within a subject, in step S1, the main control section 30 receives this and supplies control signals, for causing starting transmission of ultrasonic waves, to the transmission control section 12 and the multiplexer 11.

In step S2, the transmission control section 12 generates a driving pulse signal per channel, in accordance with control signals supplied from the main control section 30. The transmission control section 12 provides an appropriate delay time to the driving pulse signal of each channel, in order to execute transmission focusing at the region of interest within the subject. The respective driving pulse signals that are generated by the transmission control section 12 are supplied respectively to the n piezoelectric elements 10a that are selected by the multiplexer 11. Due thereto, an ultrasonic beam is transmitted toward the subject interior from the adjacent n piezoelectric elements 10a of the ultrasonic probe 10.

The echoes, that are due to reflection of the ultrasonic waves that were transmitted from the respective piezoelectric elements 10a of the ultrasonic probe 10, are received by the n piezoelectric elements 10a that were selected by the multiplexer 11 and that transmitted the ultrasonic beam. Each of the piezoelectric elements 10a generates a received signal, that is an electric signal, from the reflected echo, and outputs it via the multiplexer 11 to the received signal processing section 16. The received signal processing section 16 carries out signal processings, including amplification and A/D conversion, on the respective received signals, and stores the received signals, that have been subjected to the signal processings, in the received signal memory 17 as received data of one line in correspondence with the identification number of that line.

Thereafter, in accordance with control signals supplied from the main control section 30, the multiplexer 11 carries out switching of the piezoelectric elements 10a that are the objects of selection, and shifts, by one piezoelectric element for example, the piezoelectric elements 10a that are to carry out transmission and reception of ultrasonic waves. Thereafter, transmission and reception of ultrasonic waves are carried out in the same way as described above. Due to the multiplexer 11 successively shifting the piezoelectric elements 10a that carry out transmission and reception of ultrasonic waves, the imaging region that is within the subject is scanned by ultrasonic beams that are transmitted successively. Due thereto, received signals of plural lines (L[1], L[2], L[3] ... L[k]) that correspond to the respective transmissions are acquired, and the received signals of each line are stored in the received signal memory 17 in correspondence with the identification number of that line.

In step S3, the main control section 30 selects, from among the received signals of the respective lines that are stored in the received signal memory 17, the received signals of line L[i] (i is a positive integer that is an identification number of a line) that will be the object of the processing of deriving the degree of mutual similarity by the degree of similarity deriving section 23. The main control section 30 first selects line L[1]. Due thereto, the received signals of the first line, that were acquired by the transmission of ultrasonic waves the first time, are made to be the object of derivation of the degree of mutual similarity.

In step S4, the main control section 30 selects, from among plural set sound velocities that are set in advance, one set sound velocity C[j] (j is a positive integer that is the identification number of the set sound velocity) that is to be used in the phasing processing of the received signals carried out at the phasing processing section 18. Namely, the main control section 30 holds plural set sound velocities C[1], C[2], C[3], ..., that for example are set in steps of 10 m/s within a range of 1400 m/s to 1650 m/s, in advance and in a memory (not illustrated) that the main control section 30 itself has and in correspondence with the identification numbers of these set sound velocities. Further, the main control section 30 selects one set sound velocity from thereamong. The main control section 30 first selects set sound velocity C[1]. Due thereto, 1400 m/s is selected as the set sound velocity value that is to be used in the phasing processing. Note that the range of the set sound velocities and the width of the step are not limited to those stated above, and can be changed appropriately.

In step S5, on the basis of control signals supplied from the main control section 30, the phasing processing section 18 reads-out, from the received signal memory 17, the received signals corresponding to line L[i] that was selected by the main control section 30 in step S3. Next, on the basis of control signals supplied from the main control section 30, the phasing processing section 18 computes a reception delay time for each channel from the set sound velocity C[j] that was selected by the main control section 30 in step S4. Then, the phasing processing section 18 carries out phasing by providing the computed reception delay times to the received signals of the respective channels that were read-out from the received signal memory 17. The phasing processing section 18 supplies the phased received signals to the degree of similarity deriving section 23.

In step S6, the degree of similarity deriving section 23 sets a region that is the object of computation for which derivation of the degree of mutual similarity will be carried out on the received signals of the respective channels that have been phased. The region that is the object of computation is set by cutting-out the received signals at a given time width (a range of depth) (see FIG. 3).

Figure 3:
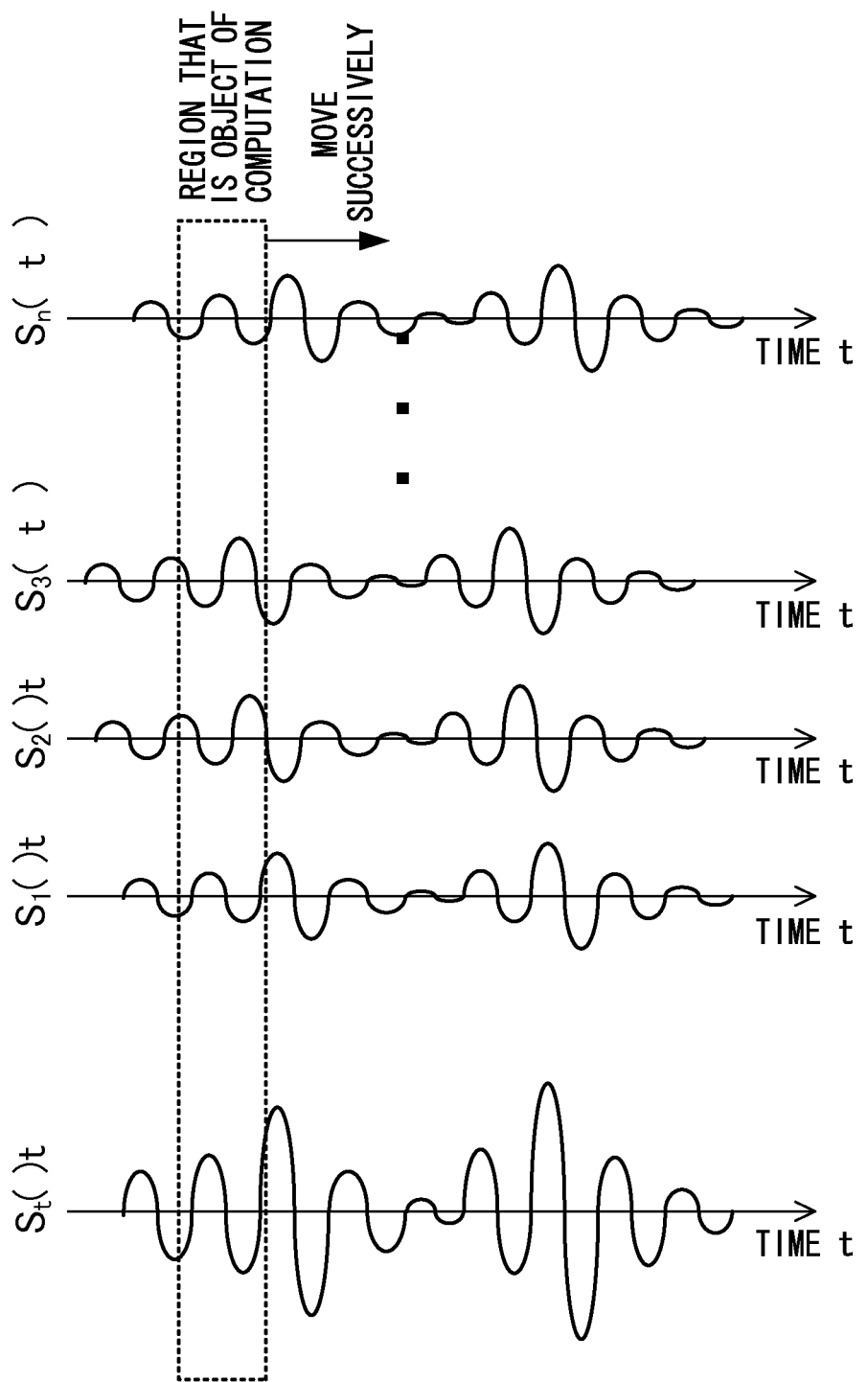
FIG. 3 is a drawing for explaining contents of processing by a degree of similarity deriving section relating to the embodiment of the present invention, and is a waveform diagram showing received signals and a template signal that have been phased on the basis of a set sound velocity.

In step S7, the degree of similarity deriving section 23 derives the degree of mutual similarity that is an index value of the similarity among the received signals of the respective channels at the region that is the object of computation that was set in step S6, and stores the derived degree of mutual similarity in a memory (not shown) that the degree of similarity deriving section 23 itself has. FIG. 3 is a waveform diagram for explaining the contents of the processing of deriving the degree of mutual similarity that is carried out by the degree of similarity deriving section 23.

Received signals $S_1(t)$ through $S_n(t)$ of the respective channels in the selected line, that were phased at the phasing processing section 18, are shown in FIG. 3. The degree of similarity deriving section 23 generates a template signal $S_t(t)$ that is a comparison reference for deriving the degree of mutual similarity among the received signals $S_1(t)$ through $S_n(t)$. The degree of similarity deriving section 23 may use, as the template signal $S_t(t)$, a phased and added signal that is obtained by summing, per same time, the received signals $S_1(t)$ through $S_n(t)$ that were phased at the set sound velocity in question.

The degree of similarity deriving section 23 computes, in accordance with following formula (1), a correlation value Ri between the template signal $S_t(t)$ and a received signal $S_i(t)$ at the region that is the object of computation that is surrounded by the dashed line in FIG. 3 (wherein i is an integer from 1 to n). In formula (1), the denominator is a value obtained by multiplying the square root of the sum of the squares of the values of the respective points of the template signal $S_t(t)$ within the region that is the object of computation, and the square root of the sum of the squares of the values of the respective points of the received signal $S_i(t)$ within the region that is the object of computation. The numerator is the sum of the values obtained by multiplying the values of the respective points of the template signal $S_t(t)$ within the region that is the object of computation and the values of the respective points of the received signal $S_i(t)$.

[Formula 1]

$$R_i = \frac{\sum \{S_t(t) \times S_i(t)\}}{\sqrt{\sum \{S_t(t)\}^2} \times \sqrt{\sum \{S_i(t)\}^2}} \quad (1)$$

The degree of similarity deriving section 23 derives correlation values $R_1, R_2, R_3 \ldots R_n$ between the received signals $S_1(t), S_2(t), S_3(t), \ldots S_n(t)$ and the template signal $S_t(t)$, respectively. Then, in accordance with following formula (2), the degree of similarity deriving section 23 derives the total sum of the absolute values of the correlation values $R_i$, that were computed for the respective received signals $S_1(t)$ through $S_n(t)$ of the respective channels, as an index value expressing the similarity among the received signals $S_1(t)$ through $S_n(t)$, i.e., as degree of mutual similarity R. The degree of mutual similarity R that is derived in this way is a value that becomes higher the closer the set sound velocity is to the actual sound velocity of the subject interior.

[Formula 2]

$$R = \sum_{i=1}^{n} Ri \quad (2)$$

Note that the above example illustrates a method of determining the degree of mutual similarity R by computing the correlation values between the template signal $S_t(t)$ and the received signals $S_1(t)$ through $S_n(t)$ of the respective channels, respectively. However, the present invention is not limited to this. For example, the correlation values $R_i$ may respectively be determined in accordance with following formula (3) between received signals that are adjacent to one another (i.e., $S_i(t)$ and $S_{i+1}(t)$), and the total sum of the absolute values thereof may be derived as the degree of mutual similarity R. In this case, there is no need to generate the template signal $S_t(t)$, and therefore, it is possible to increase the speed of the computing processing.

[Formula 3]

$$R_i = \frac{\sum \{S_i(t) \times S_{i+1}(t)\}}{\sqrt{\sum \{S_i(t)\}^2} \times \sqrt{\sum \{S_{i+1}(t)\}^2}} \quad (3)$$

In step S8, the degree of similarity deriving section 23 judges whether or not deriving of the degree of mutual similarity has been completed for the entire depth range of the received signal (the entire time range). If the degree of similarity deriving section 23 judges in the present step that deriving of the degree of mutual similarity has not been completed, the degree of similarity deriving section 23 returns to step S6 and shifts the region that is the object of computation in the time axis direction (the depth direction), and sets a new region that is the object of computation, and, in the same way as described above, derives a degree of mutual similarity for this region that is the object of computation. The degree of similarity deriving section 23 repeats the processings of steps S6 through S8 until deriving of degrees of mutual similarity is completed for the entire time range (the entire depth range) of the received signals.

In step S9, the main control section 30 increments, by 1, the identification number j of the set sound velocity C[j]. In step S10, by comparing the incremented numerical value j with a maximum value Jmax of the identification numbers j of the set sound velocities, the main control section 30 judges whether or not deriving of the degrees of mutual similarity has been completed for all of the set sound velocities. If the main control section 30 judges in step S10 that deriving of the degrees of mutual similarity has not been completed for all of the set sound velocities, processing is returned to step S4, a new set sound velocity is set, and the processings of steps S5 through S10 are carried out in the same way. Due to the main control section 30 successively incrementing the identification number j of the set sound velocity C[j], the degrees of mutual similarity among the received signals are derived for the respective received signal groups that have been phased on the basis of the respective set sound velocities within the range of 1400 m/s through 1650 m/s.

In step S11, the main control section 30 increments, by 1, the identification number i of the line L[i] of received signals corresponding to each transmission of ultrasonic waves. In step S12, by comparing the incremented numerical value i and a numerical value k that expresses the maximum value of the identification numbers i, the main control section 30 judges whether or not deriving of the degrees of mutual similarity has been completed for all of the lines. If the main control section 30 judges in step S12 that deriving of the degrees of mutual similarity has not been completed for all of the lines, processing returns to step S3, and a new line that is to be the object of deriving of the degree of mutual similarity is selected, and the processings of steps S4 through S12 are carried out in the same way. Due to the main control section 30 successively incrementing the identification number i of the line L[i], the degrees of mutual similarity can be derived per set sound velocity and per region that is the object of computation in the same way as described above, for the received signals of each line.

Figure 4:
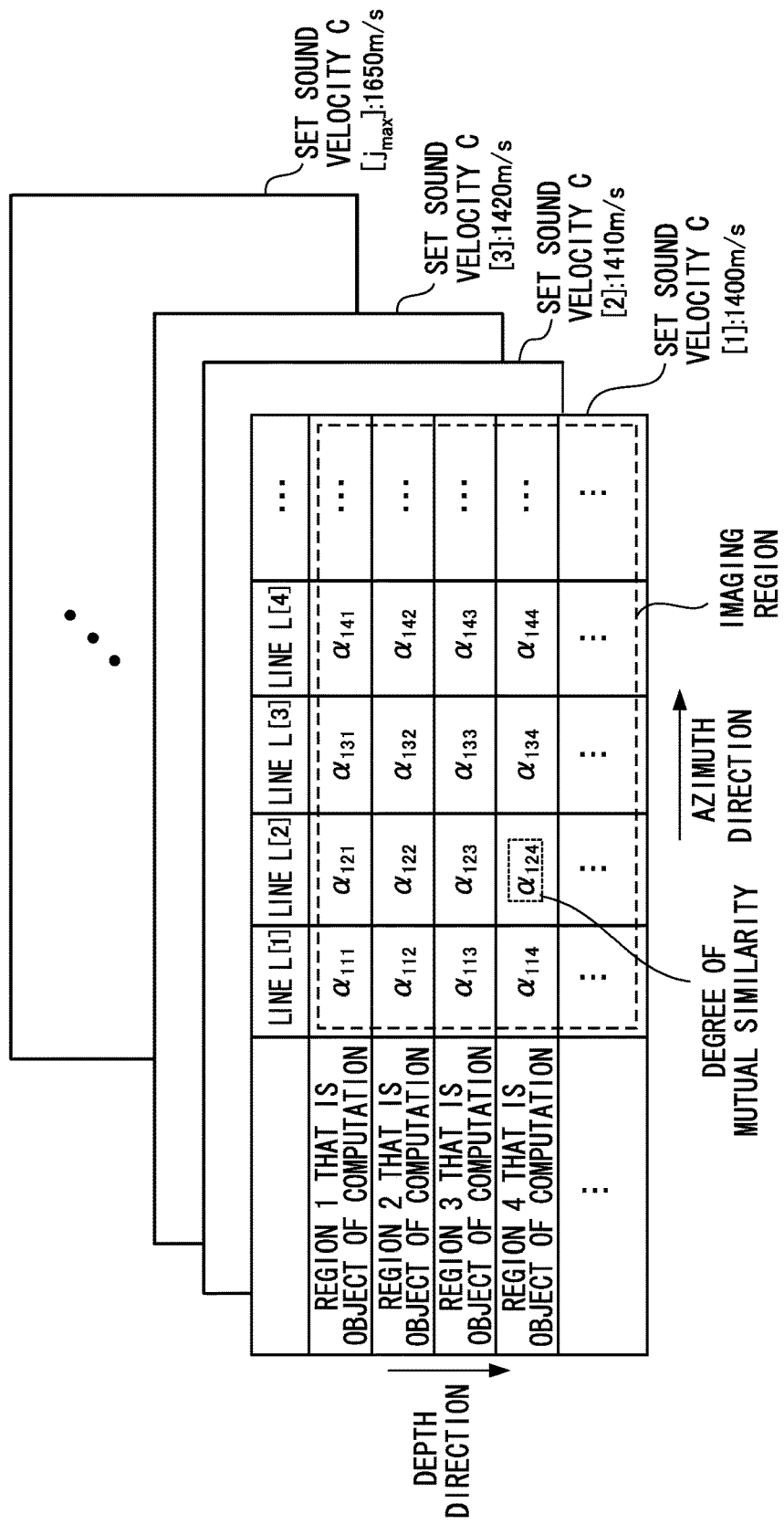
FIG. 4 is a schematic drawing showing a storage format of degrees of similarity that are derived by the degree of similarity deriving section relating to the embodiment of the present invention.

The degree of similarity deriving section 23 stores the respective degrees of mutual similarity of the received signal groups that were derived through the above-described respective processings, in a memory (not illustrated) that the degree of similarity deriving section 23 itself has and in a form such as shown in FIG. 4. $\alpha_{111}$, $\alpha_{112}$, $\alpha_{113}$, ... that are shown in FIG. 4 are the degrees of mutual similarity at the respective regions that are the object of computation (the respective depth positions) of the respective lines that were derived per set sound velocity. As shown in FIG. 4, the degree of similarity deriving section 23 derives a degree of mutual similarity at a unit region, that is obtained by dividing the imaging region by respective lines and respective depth positions, for the respective cases in which the respective set sound velocities C[1], C[2], C[3] ... are set.

In step S13, the optimal set sound velocity deriving section 24 reads-out, from the memory within the degree of similarity deriving section 23, the degrees of mutual similarity that were derived by the degree of similarity deriving section 23, and, on the basis of the read-out degrees of mutual similarity, derives an optimal set sound velocity within the subject. For example, the optimal set sound velocity deriving section 24 derives a set sound velocity, at which the degree of mutual similarity of the received signal group that was derived for a given depth of a given line becomes a maximum, as the optimal set sound velocity at that depth position of that line.

The optimal set sound velocity deriving section 24 supplies the optimal set sound velocity, that was derived in this way, to the main control section 30, and the present routine ends.

Figure 5:
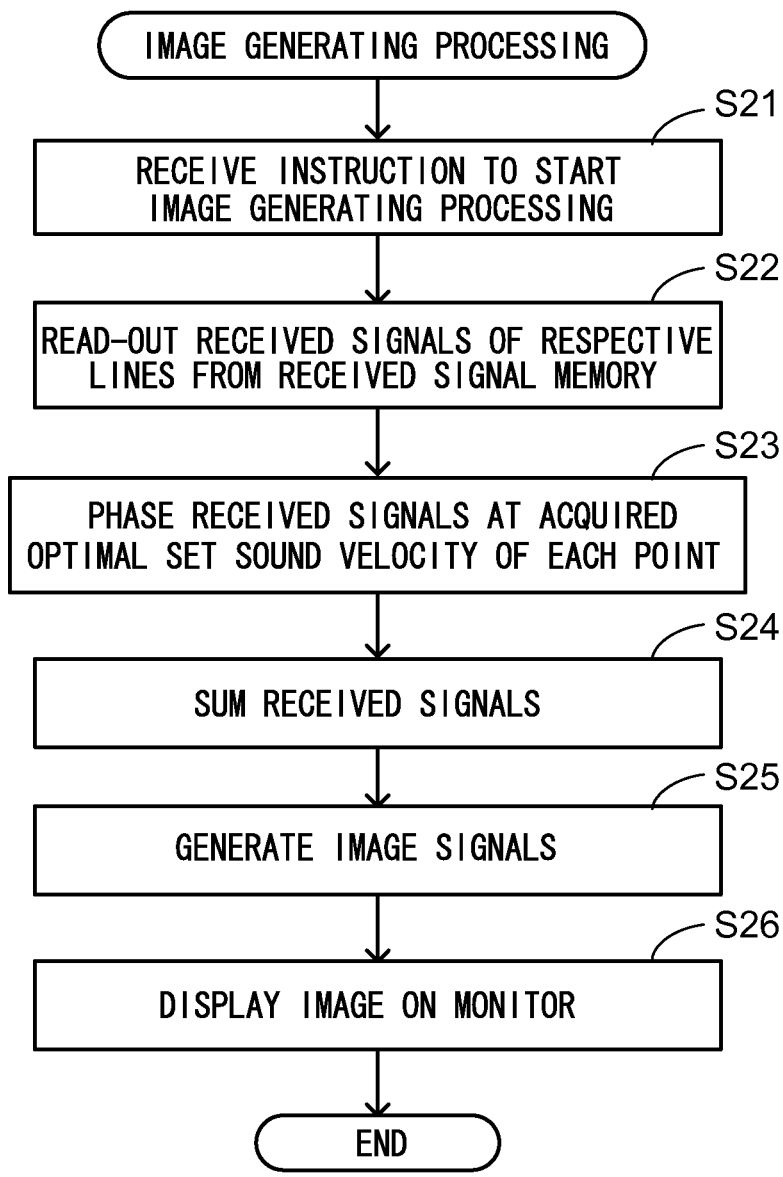
FIG. 5 is a flowchart showing the flow of an image generating processing program that is executed at the ultrasonic diagnostic device relating to the embodiment of the present invention.

An example of image generating processing using the optimal set sound velocity that was derived for each region within the imaging region, is described hereinafter with reference to the flowchart shown in FIG. 5.

In step S21, in accordance with an operation input from the operation input portion 40 by the user for example, the main control section 30 supplies, to the phasing processing section 18, the optimal set sound velocities at the respective depth positions of the respective lines that were derived by the optimal set sound velocity deriving section 24, and the phasing processing section 18 receives these.

In step S22, the phasing processing section 18 reads-out the received signals of the respective lines from the received signal memory 17.

In step S23, on the basis of the optimal set sound velocities at the respective points that were derived by the optimal set sound velocity deriving section 24, the phasing processing section 18 computes a reception delay time at each point, and provides the computed reception delay times to the received signals read-out from the received signal memory 17, and carries out phasing processing. The phasing processing section 18 supplies the phased received signals to the addition processing section 20.

In step S24, the addition processing section 20 sums the received signals of the respective channels that were phased by the phasing processing section 18, and generates a phased and added signal, and supplies this to the image generating section 21.

In step S25, the image generating section 21 carries out filtering processing, Log compression processing, envelope detection processing, STC processing, interpolation processing, scan conversion processing, and the like on the phased and added signals that are supplied from the addition processing section 20, and generates image signals for constructing B-mode images in which the signal intensities of the phased and added signals are converted into brightnesses. The image generating section 21 supplies the generated image signals to the monitor 22.

In step S26, the monitor 22 displays the image signals that were generated by the image generating section 21.

By going through the above-described respective processings, the present image generating processing routine ends.

As is clear from the above explanation, the ultrasonic diagnostic device 1 relating to the present embodiment derives degrees of mutual similarity that are index values of the similarity among received signals of respective channels that have been phased at respective set sound velocities, and derives an optimal set sound velocity on the basis of the derived degrees of mutual similarity. Namely, at the time of deriving the optimal set sound velocity, there is no need for processing that makes the received signals into images, and therefore, deriving of the optimal set sound velocity in a relatively short time is possible. Further, in accordance with the ultrasonic diagnostic device 1 relating to the present embodiment, the optimal set sound velocity is derived on the basis of the degree of mutual similarity among the received signals of each channel. Therefore, even when a decrease in intensity of or waveform distortion of the received signals arises due to interference of ultrasonic waves within the subject or the like, the degree of mutual similarity itself does not fluctuate greatly, and thus, the optimal set sound velocity can be derived relatively stably, and the accuracy of deriving the optimal set sound velocity can be increased. Namely, the error between the optimal set sound velocity and the actual sound velocity can be made to be small. Further, in accordance with the ultrasonic diagnostic device 1 relating to the present embodiment, images are generated from received signals that have been phased by using optimal set sound velocities that have been derived with high accuracy, and therefore, tomographic images with little distortion can be generated.

Note that, in the above-described embodiment, the optimal set sound velocity is derived for each depth position of each line, but the present invention is not limited to this. The optimal set sound velocity deriving section 24 may, for each block that is formed from plural depth positions of plural lines, compute a total sum $\alpha_{SUM}$ of the degrees of mutual similarity of the received signals of the respective depth positions of the respective lines within that block, and derive the set sound velocity, at which the value of $\alpha_{SUM}$ is the greatest, as the optimal set sound velocity at that block.

Further, in the above-described embodiment, the set sound velocity at which the degree of mutual similarity is the maximum is made to be the optimal set sound velocity at that region, but the present invention is not limited to this. The optimal set sound velocity deriving section 24 may derive a value, that is obtained by computing a weighted average value in which the respective set sound velocities are weighted by the degrees of mutual similarity of the received signals, as the optimal set sound velocity at that region.

Further, the above description illustrates, as an example, a case in which the degree of similarity deriving section 23 computes a one-dimensional correlation value between the template signal and the received signals of the respective channels. However, the present invention is not limited to this. The degree of similarity computing section 23 may compute a two-dimensional correlation value by expanding the template signal into a two-dimensional signal in the direction of the piezoelectric elements and the time axis direction (the depth direction). Namely, two-dimensional template signals $S_{t1}(1)$, $S_{t2}(t)$, ... $S_{tm}(t)$, in which the template signals $S_t(t)$ are lined-up in correspondence with the received signals of the respective channels, may be generated (here, $S_{t1}(t)=S_{t2}(t)=\ldots=S_{tm}(t)$), and two dimensional correlation values between these and the received signals $S_1(t)$ through $S_n(t)$ of the respective channels may be derived in accordance with following formula (4) and made to be the correlation value R. Here, $\Sigma$ represents the summation relating to t (the time axis direction) and i (the direction of the piezoelectric elements).

[Formula 4]

$$R_i = \frac{\sum \{S_{ti}(t) \times S_i(t)\}}{\sqrt{\sum \{S_{ti}(t)\}^2} \times \sqrt{\sum \{S_i(t)\}^2}} \quad (4)$$

Further, in the case of using a three-dimensional probe, a three-dimensional correlation value may be computed.

Further, the degree of similarity deriving section 23 may carry out mutual correlation computation on the template signal St(t) and the respective received signals $S_1(t)$ through $S_n(t)$ respectively, and determine phase shift amounts of the respective received signals $S_1(t)$ through $S_n(t)$ with respect to the template signal $S_t(t)$ from the position at which the peak value of the determined mutual correlation function exists, and derive, as the index value of the similarity among the received signals, the total sum or the variance of the absolute values of the phase shift amounts determined for the respective received signals $S_1(t)$ through $S_n(t)$. In this case, the greater the similarity among the received signals, the smaller the derived value.

Further, in the above-described embodiment, the degree of similarity is derived by using the received signals after they have undergone phasing processing. However, the present invention is not limited to this. For the received signals of the respective channels, a region that is the object of computation, that is centered around reception delay times that are computed for the received signals of the respective channels on the basis of the set sound velocity, may be derived, and the degree of mutual similarity among the received signals within each region that is the object of computation may be derived.

The disclosure of Japanese Patent Application No. 2012-120242 is, in its entirety, incorporated by reference into the present specification.

All publications, patent applications, and technical standards mentioned in the present specification are incorporated by reference into the present specification to the same extent as if each individual publication, patent application, or technical standard was specifically and individually indicated to be incorporated by reference.

The above-described ultrasonic diagnostic device may be structured so as to further include a phasing section for, for each of the plural set sound velocities, phasing plural received signals that were generated at plural electroacoustic conversion elements respectively among the plural electroacoustic conversion elements, wherein the degree of similarity deriving section derives a degree of mutual similarity among the received signals that were phased by the phasing section.

The degree of similarity deriving section may derive the degree of mutual similarity on the basis of correlation values between a reference signal and each of the received signals that were phased by the phasing section. In this case, the degree of similarity deriving section may derive, as the degree of mutual similarity, a value obtained by summing the correlation values between the reference signal and each of the received signals that were phased by the phasing section.

The reference signal can be made to be a phased and added signal obtained by summing the respective received signals that were phased.

The degree of similarity deriving section may derive the degree of mutual similarity on the basis of correlation values between received signals that are adjacent to one another and that were phased by the phasing section. In this case, the degree of similarity deriving section may derive, as the degree of mutual similarity, a value obtained by summing the correlation values between received signals that are adjacent to one another and that were phased by the phasing section.

The sound velocity deriving section may derive a set sound velocity, at which the degree of mutual similarity is a maximum, as an estimated value of sound velocity of the subject interior.

The optimal set sound velocity deriving section may derive, as an estimated value of a sound velocity of the subject interior, a weighted average value that is obtained by weighting the respective set sound velocities by the degree of mutual similarity.

The phasing section may phase the received signals on the basis of the estimated value of sound velocity of the subject interior that was derived by the sound velocity deriving section, an adding section may sum the respective received signals that were phased by the phasing section and generate a phased and added signal, and an image generating section may generate images that correspond to the phased and added signals.

In accordance with the ultrasonic diagnostic device, sound velocity deriving method and computer-readable storage medium relating to the present invention, more stable and highly-accurate derivation of an estimated value of sound velocity of a subject interior is possible.

What is claimed is:

1. An ultrasonic diagnostic device comprising:
electroacoustic conversion elements configured to respectively generate received signals in accordance with reflected waves of ultrasonic waves that were transmitted to a subject interior, wherein each of the received signals is generated by a respective electroacoustic conversion element of the electroacoustic conversion elements;
a degree of similarity deriving section configured to derive, for each respective sound velocity of a plurality of set sound velocities, a degree of mutual similarity that expresses similarity among the received signals of the respective electroacoustic conversion elements, on the basis of reception delay times computed from the respective sound velocity; and
a sound velocity deriving section configured to derive an estimated value of sound velocity of the subject interior on the basis of each degree of mutual similarity for each respective sound velocity of the plurality of set sound velocities that was derived by the degree of similarity deriving section.

2. The ultrasonic diagnostic device of claim 1, further comprising a phasing section configured to, for each respective sound velocity of the plurality of set sound velocities, respectively phase the received signals of the respective electroacoustic conversion elements by applying the computed reception delay times computed from the respective sound velocity,
wherein the degree of similarity deriving section is further configured to derive each degree of mutual similarity, for each respective sound velocity of the plurality of set sound velocity, by calculating a mutual similarity among the received signals of the respective electroacoustic conversion elements that were respectively phased by the phasing section for each respective sound velocity of the plurality of set sound velocity.

3. The ultrasonic diagnostic device of claim 2, wherein the degree of similarity deriving section is further configured to
calculate respective correlation values between a reference signal and each signal of the received signals of the respective electroacoustic conversion elements that were respectively phased by the phasing section for each respective sound velocity of the plurality of set sound velocities, and
derive each degree of mutual similarity respectively on the basis of the respective correlation values.

4. The ultrasonic diagnostic device of claim 3, wherein the degree of similarity deriving section is further configured to
calculate, for each respective sound velocity of the plurality of set sound velocities, a respective summation value by summing the respective correlation values, and
derive each degree of mutual similarity on the basis of the respective summation value.

5. The ultrasonic diagnostic device of claim 3, wherein the degree of similarity deriving section is further configured to respectively obtain the reference signal by summing the received signals of the respective electroacoustic conversion elements that were respectively phased by the phasing section for each respective sound velocity of the plurality of set sound velocities.

6. The ultrasonic diagnostic device of claim 4, wherein the degree of similarity deriving section is further configured to respectively obtain the reference signal by summing the received signals of the respective electroacoustic conversion elements that were respectively phased by the phasing section for each respective sound velocity of the plurality of set sound velocities.

7. The ultrasound diagnostic device of claim 2, further comprising a multiplexer configured to select, from among the received signals of the respective electroacoustic conversion elements, adjacent signals that were generated by a subset of the electroacoustic conversion elements that are adjacent to one another,
wherein the phasing section is further configured to, for each respective sound velocity of the plurality of set sound velocities, respectively phase the adjacent signals by applying the computed reception delay times computed from the respective sound velocity,
wherein the degree of similarity deriving section is further configured to:
calculate respective correlation values between the adjacent signals that were respectively phased by the phasing section for each respective sound velocity of the plurality of set sound velocities, and derive each degree of mutual similarity on the basis of the respective correlation values.

8. The ultrasonic diagnostic device of claim 7, wherein the degree of similarity deriving section is further configured to:
calculate, for each respective sound velocity of the plurality of set sound velocities, a respective summation value by summing the respective correlation values, and
derive each degree of mutual similarity on the basis of the respective summation value.

9. The ultrasonic diagnostic device of claim 1, wherein the sound velocity deriving section is further configured to derive the estimated value of sound velocity of the subject interior by identifying a respective sound velocity of the plurality of set sound velocities at which the degree of mutual similarity is a maximum.

10. The ultrasonic diagnostic device of claim 2, wherein the sound velocity deriving section is further configured to derive the estimated value of sound velocity of the subject interior by identifying a respective sound velocity of the plurality of set sound velocities at which the degree of mutual similarity is a maximum.

11. The ultrasonic diagnostic device of claim 3, wherein the sound velocity deriving section is further configured to derive the estimated value of sound velocity of the subject interior by identifying a respective sound velocity of the plurality of set sound velocities at which the degree of mutual similarity is a maximum.

12. The ultrasonic diagnostic device of claim 1, wherein the sound velocity deriving section is further configured to derive said estimated value of sound velocity of the subject interior by calculating a weighted average sound velocity value,
wherein the weighted average sound velocity is calculated by weighting each respective sound velocity of the plurality of set sound velocities by each degree of mutual similarity respectively, and calculating an average thereof.

13. The ultrasonic diagnostic device of claim 2, wherein the sound velocity deriving section is further configured to derive said estimated value of sound velocity of the subject interior by calculating a weighted average sound velocity value,
wherein the weighted average sound velocity is calculated by weighting each respective sound velocity of the plurality of set sound velocities by each degree of mutual similarity respectively, and calculating an average thereof.

14. The ultrasonic diagnostic device of claim 3, wherein the sound velocity deriving section is further configured to derive, said estimated value of sound velocity of the subject interior by calculating a weighted average sound velocity value,
wherein the weighted average sound velocity is calculated by weighting each respective sound velocity of the plurality of set sound velocities by each degree of mutual similarity respectively, and calculating an average thereof.

15. The ultrasonic diagnostic device of claim 2, wherein the phasing section is further configured to generate improved phased signals by phasing the received signals of the respective electroacoustic conversion elements on the basis of the estimated value of sound velocity of the subject interior that was derived by the sound velocity deriving section, and wherein the ultrasonic diagnostic device further comprises:
an adding section configured to generate a phased and added signal by summing the improved phased signals, and
an image generating section configured to generate an image from the phased and added signal.

16. The ultrasonic diagnostic device of claim 3, wherein the phasing section is further configured to generate improved phased signals by phasing the received signals of the respective electroacoustic conversion elements on the basis of the estimated value of sound velocity of the subject interior that was derived by the sound velocity deriving section, and wherein the ultrasonic diagnostic device further comprises:
an adding section configured to generate a phased and added signal by summing the improved phased signals, and
an image generating section configured to generate an image from the phased and added signal.

17. The ultrasonic diagnostic device of claim 7, wherein the phasing section is further configured to generate improved phased signals by phasing the received signals of the respective electroacoustic conversion elements on the basis of the estimated value of sound velocity of the subject interior that was derived by the sound velocity deriving section, and wherein the ultrasonic diagnostic device further comprises:
an adding section configured to generate a phased and added signal by summing the improved phased signals, and
an image generating section configured to generate an image from the phased and added signal.

18. A sound velocity deriving method comprising:
obtaining a received signals respectively generated by electroacoustic conversion elements in accordance with reflected waves of ultrasonic waves transmitted to a subject interior, wherein each of the received signals is generated by a respective electroacoustic conversion element of the electroacoustic conversion elements;
phasing, for each respective sound velocity of a plurality of set sound velocities, the received signals of respective electroacoustic conversion elements by applying reception delay times computed from the respective sound velocity;
deriving, for each respective sound velocity of the plurality of set sound velocities, a degree of mutual similarity that expresses similarity among the phased received signals of the respective electroacoustic conversion elements; and
deriving an estimated value of sound velocity of the subject interior on the basis of each degree of mutual similarity for each respective sound velocity of the plurality of set sound velocities.

19. A non-transitory computer-readable storage medium storing a program that, when executed by a computer, causes the computer to perform a method, the method comprising:
receiving or storing received signals respectively generated by electroacoustic conversion elements in accordance with reflected waves of ultrasonic waves transmitted to a subject interior, wherein each of the received signals is generated by a respective electroacoustic conversion element of the electroacoustic conversion elements
phasing, for each respective velocity of a plurality of set sound velocities, the received signals of the respective electroacoustic conversion elements by applying reception delay times computed from the respective sound velocity;

deriving, for each respective sound velocity of the plurality of set sound velocities, a degree of mutual similarity that expresses similarity among the phased received signals of the respective electroacoustic conversion elements; and deriving an estimated value of sound velocity of the subject interior on the basis of each derived degree of mutual similarity for each respective sound velocity of the plurality of set sound velocities.

* * * * *